United States Patent
Marashdeh

(10) Patent No.: US 10,512,415 B2
(45) Date of Patent: *Dec. 24, 2019

(54) MULTI-PHASE FLOW DECOMPOSITION USING ELECTRICAL CAPACITANCE VOLUME TOMOGRAPHY SENSORS

(71) Applicant: Tech4Imaging LLC, Columbus, OH (US)

(72) Inventor: Qussai Marashdeh, Columbus, OH (US)

(73) Assignee: Tech4Imaging LLC, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/371,804

(22) Filed: Apr. 1, 2019

(65) Prior Publication Data

US 2019/0223752 A1    Jul. 25, 2019

Related U.S. Application Data

(63) Continuation of application No. 15/885,287, filed on Jan. 31, 2018, now Pat. No. 10,244,962, which is a
(Continued)

(51) Int. Cl.
*G01R 27/26* (2006.01)
*A61B 5/053* (2006.01)
(Continued)

(52) U.S. Cl.
CPC ............ *A61B 5/0536* (2013.01); *A61B 5/004* (2013.01); *A61B 5/1076* (2013.01); *G01F 1/708* (2013.01);
(Continued)

(58) Field of Classification Search
CPC .. G01N 27/221; G01N 27/226; G01N 27/228; G01N 27/2623; G01N 27/2617;
(Continued)

(56) References Cited

U.S. PATENT DOCUMENTS 5,130,661 A    7/1992  Beck et al.
5,262,730 A    11/1993 Smith et al.
(Continued)

FOREIGN PATENT DOCUMENTS

CN    102954854 A    3/2013
EP    0606115 A1    7/1994
(Continued)

OTHER PUBLICATIONS

Chew, W. et al., Reconstruction of Two-Dimensional Permittivity Distribution Using the Distorted Born Iterative Method, IEEE Transactions on Medical Imaging, Jun. 1990, pp. 218-225, vol. 9, No. 2.
(Continued)

*Primary Examiner* — Thang X Le
(74) *Attorney, Agent, or Firm* — Standley Law Group LLP

(57) ABSTRACT

The present invention provides a system and method for multi-phase flow decomposition using electrical capacitance imaging techniques. The present invention provides a system and method to obtain permittivity distributions at a plurality of frequency markers using volume tomography image reconstruction to determine volume fraction of each phase and to produce images of the volume fraction for each phase.

14 Claims, 8 Drawing Sheets

Related U.S. Application Data continuation of application No. 15/138,751, filed on Apr. 26, 2016, now Pat. No. 9,901,282.

(60) Provisional application No. 62/153,095, filed on Apr. 27, 2015.

(51) Int. Cl.
| | | |
|---|---|---|
| *G01N 27/22* | (2006.01) | |
| *A61B 5/107* | (2006.01) | |
| *A61B 5/00* | (2006.01) | |
| *G01F 1/708* | (2006.01) | |
| *G01F 1/74* | (2006.01) | |
| *A61B 5/02* | (2006.01) | |

(52) U.S. Cl.
CPC .............. *G01F 1/74* (2013.01); *G01N 27/221* (2013.01); *G01R 27/2623* (2013.01); *A61B 5/02007* (2013.01); *A61B 2562/0214* (2013.01)

(58) Field of Classification Search
CPC .... G01N 27/24; A61B 5/0536; A61B 5/1076; A61B 327/681
See application file for complete search history.

(56) References Cited

U.S. PATENT DOCUMENTS

| | | | |
|---|---|---|---|
| 6,208,204 B1 | 3/2001 | Suzuki et al. | |
| 7,424,462 B2 | 9/2008 | Avni et al. | |
| 7,684,846 B2 | 3/2010 | Johnson et al. | |
| 8,461,852 B2 | 6/2013 | Yang et al. | |
| 8,508,238 B2 * | 8/2013 | Mahalingam | A61B 5/0536 324/603 |
| 8,519,722 B1 | 8/2013 | Prendergast | |
| 8,614,707 B2 | 12/2013 | Warsito et al. | |
| 8,867,928 B2 | 10/2014 | Piehler | |
| 9,016,143 B2 | 4/2015 | Mamigonians | |
| 9,170,224 B2 | 10/2015 | Fan et al. | |
| 9,259,168 B2 | 2/2016 | Marashdeh et al. | |
| 9,535,026 B2 | 1/2017 | Marashdeh et al. | |
| 9,579,038 B2 | 2/2017 | Brunner et al. | |
| 9,581,560 B2 | 2/2017 | Fan et al. | |
| 2002/0028010 A1 | 3/2002 | Toida | |
| 2003/0020493 A1 | 1/2003 | Haase et al. | |
| 2003/0173958 A1 | 9/2003 | Goldfine et al. | |
| 2004/0233191 A1 | 11/2004 | Mukherjee et al. | |
| 2005/0167588 A1 | 8/2005 | Donnangelo | |
| 2007/0024278 A1 | 2/2007 | Walters et al. | |
| 2007/0133746 A1 | 6/2007 | Ortiz Aleman et al. | |
| 2008/0116995 A1 | 5/2008 | Kim et al. | |
| 2009/0272028 A1 | 11/2009 | Drozd et al. | |
| 2010/0097374 A1 * | 4/2010 | Fan | A61B 5/0535 345/420 |
| 2010/0132473 A1 | 6/2010 | Willcox | |
| 2010/0148804 A1 | 6/2010 | Jakoby et al. | |
| 2010/0332170 A1 | 12/2010 | Gao et al. | |
| 2011/0109911 A1 | 5/2011 | Podoleanu | |
| 2012/0268135 A1 | 10/2012 | Marsala et al. | |
| 2013/0187641 A1 | 7/2013 | Singer | |
| 2013/0275082 A1 | 10/2013 | Follmer et al. | |
| 2013/0327154 A1 * | 12/2013 | Xie | G01N 22/00 73/861.04 |
| 2014/0361793 A1 | 12/2014 | Marashdeh et al. | |
| 2014/0365009 A1 | 12/2014 | Wettels | |
| 2014/0365152 A1 | 12/2014 | Marashdeh et al. | |
| 2015/0048852 A1 | 2/2015 | Marshdeh et al. | |
| 2015/0338364 A1 * | 11/2015 | Fan | G01N 27/026 324/663 |
| 2016/0076926 A1 | 3/2016 | McCann et al. | |
| 2016/0091448 A1 | 3/2016 | Soleimani | |
| 2016/0206227 A1 * | 7/2016 | Marashdeh | A61B 5/05 |
| 2016/0310040 A1 | 10/2016 | Marashdeh | |
| 2016/0327503 A1 | 11/2016 | Marashdeh et al. | |

FOREIGN PATENT DOCUMENTS

| | | |
|---|---|---|
| WO | 2010007096 A3 | 1/2010 |
| WO | 2011002793 A1 | 1/2011 |

OTHER PUBLICATIONS

Huang et al., Design of Sensor Electronics for Electrical Capacitance Tomography, IEE Proceedings G (Circuits, Devices and Systems), vol. 139, Issue 1, Feb. 1992, p. 83-88.

Marashdeh, Q. et al., Adaptive Electrical Capacitance Volume Tomography, IEEE Sensors Journal, Apr. 2014, pp. 1253-1259, vol. 14, No. 4.

Xie, C. et al., Electrical Capacitance Tomography for Flow Imaging: System Model for Development of Image Reconstruction Algorithms and Design of Primary Sensors, IEEE Proceedings-G, Feb. 1992, pp. 89-98, vol. 139, No. 1.

Yang, W. et al., Image Reconstruction Algorithms for Electrical Capacitance Tomography, Measurement Science and Technology 14, 2003, pp. R1-R13.

Marashdeh, et al., "On the ECT Sensor Based Dual Imaging Modality System for Electrical Permittivity and Conductivity Measurements", 2006, pp. 1-6, The Ohio State University, Columbus, Ohio.

Warsito, et al., "Electrical Capacitance Volume Tomography", 2007, pp. 1-9.

Covilakam, M., "Evaluation of Structural Monitoring Methods for Large Diameter Water Transmission Pipelines", Dec. 2011, The University of Texas at Arlington.

* cited by examiner

MULTI-PHASE FLOW DECOMPOSITION USING ELECTRICAL CAPACITANCE VOLUME TOMOGRAPHY SENSORS

CROSS-REFERENCE TO RELATED APPLICATIONS

This application is a continuation of U.S. application Ser. No. 15/885,287, filed Jan. 31, 2018, which is a continuation of U.S. application Ser. No. 15/138,751, filed Apr. 26, 2016, which claims priority to U.S. Provisional Application No. 62/153,095, filed on Apr. 27, 2015. Each of which is incorporated by reference as if fully recited herein.

BACKGROUND AND SUMMARY OF THE INVENTIVE FIELD

Multi-phase flow systems are the interaction between materials in which each has distinct and homogenous physical properties. Each component in the flow that is homogenous in its physical properties and separable is referred to as Phase. In a flow system, phase measurement is important to properly optimize, control, and predict multiphase flow systems. Phase physical properties that are required to optimize of measure a multiphase process are phase distribution, velocity, and mass flow rate. It is desired to obtain such measurements for each phase individually while all phases are interacting in a multiphase flow system. For example, for a multiphase flow system consisting of gas, liquid, and solid particles, measured information of each individual phase is needed to properly control and understand the flow system.

Electrical capacitance sensors use the difference in dielectric constants between phases to measure a capacitance signal. The capacitance signal is a measure of the effective dielectric constant for the mixture of phases. From the measured effective dielectric constant, phase concentrations are inferred. This technique is most effective when the multiphase flow contains only two phases. For three or more phases, it is difficult to identify each phase concentration from a single capacitance measurement.

In the present invention, a method is devised to measure three or more phases in a multiphase flow system by exploiting the Maxwell-Wagner-Sillars (MWS) polarization effect, and using a capacitance sensor. The MWS effect is the change in effective dielectric of a mixture where at least one phase is conductive. Although each phase would have a relatively fixed dielectric constant at frequencies in the quasi-static range, the mixture would have a frequency dependent effective dielectric constant.

Typically, the transition in the frequency domain at which the effective dielectric constant changes depends on the electric properties of the conductive phase that is causing this effect. For mixtures that have multiple phases, multiple frequency transitions may occur where each frequency transition would be related to a phase in the mixture. Measuring capacitance at frequencies higher and lower relative to the transition point provides a measurement that is specifically related to the phase that caused this transition. In other words, a multiphase flow system can be decomposed to its individual phases where each phase is measured distinctly.

This multiphase decomposition approach can be extended to imaging of each phase distribution, distinctly, by using multiple capacitance sensors in formations that provide a tomography measurement. Here, Electrical Capacitance Tomography (ECT) is the reconstruction of material concentrations of dielectric physical properties in the imaging domain by inversion of capacitance data from a capacitance sensor.

Electrical Capacitance Volume Tomography or ECVT is the direct 3D reconstruction of volume concentration or physical properties in the imaging domain utilizing 3D features in the ECVT sensor design. ECVT technology is described in U.S. Pat. No. 8,614,707 to Warsito et al. which is hereby incorporated by reference.

Adaptive Electrical Capacitance Volume Tomography (AECVT) provides higher resolution volume imaging of capacitance sensors based on different levels of activation levels on sensor plate segments. AECVT is described in U.S. Patent Application Publication US2013/0085365 A1 to Marashdeh et al. which is hereby incorporated by reference.

In ECT, ECVT, or AECVT, the capacitance measurement between sensor plates are also related to the effective dielectric content between that plate pair. The phase's decomposition method can be extended to all measurements of ECT, ECVT, or AECVT sensors, thus providing a visual representation of each phase, alone, through image reconstruction.

The relationship between effective dielectric constant and operating frequency is described in several empirical and theoretical approaches that incorporate each phase volume fraction and electrical properties. As each phase electrical properties are known or can be measured, it is the dynamic volume fraction distribution that is sought in multi-phase flow imaging. Here, the instantaneous phase distribution and volume fraction is sought. Among the most notable formulations that relate effective dielectric constant to each phase electric properties and volume fraction are the Wiener, Bruggeman, and Wagner formulations. Those formulations, and all others, take the electric properties of each phase and their volume fraction as inputs to estimate the effective dielectric constant. The available different formulations are related to the nature of the mixing between phases. For example, a system where all phases are homogenously mixed has a different formulation than a system where phases are layered. Nevertheless, all formulations use the same inputs to infer the effective dielectric constant. All effective dielectric constant formulations can be summarized as:

$$\varepsilon_{effective} = f((\in'_1, \sigma_1, \varphi_1), (\in'_2, \sigma_2, \varphi_2) \ldots (\in'_n, \sigma_n, \varphi_a), \omega))$$

Where f is the formulation function, n is the number of phases in the multi-phase flow system, $\omega$ is the angular frequency at which capacitance is being measured, and ($\in'_n$, $\sigma_n$, $\varphi_n$) are the complex permittivity, conductivity, and volume fraction of the nth phase, respectively.

Using the effective permittivity formulation, capacitance sensors can be used to image each phase individually in this invention of multi-Phase flow decomposition. As measured capacitance is linearly related to the effective dielectric constant between capacitance plates used to measure capacitance, developed formulation for effective dielectric constants can be used to isolate each phase. Specifically, multiple capacitance measurements are taken at different frequencies. Capacitance acquired using an ECT, ECVT, or AECVT sensor at a single frequency is used to reconstruct an effective permittivity map. As capacitance is acquired at multiple frequencies, a number of permittivity images equal to the number of frequencies will be available. Here, we assume each pixel in the image is a well-mixed region of all phases in the multi-phase flow. The volume fraction of each phase in every pixel is calculated by solving a number of equations equal to the number of phases. Those equations are obtained from formulations that related effective dielectric constant at each frequency.

A data acquisition system operating at multiple frequencies is required for phase decomposition. Capacitances can be measured at different frequencies successively or simultaneously. In the former approach, the data acquisition speed of capacitance values at different frequencies should be higher than flow speed. In the latter, a synchronous demodulator is used to isolate each capacitance value related to each frequency. Using both measuring schemes, the difference between measured capacitances (successive or simultaneous) is used to isolate the change in effective dielectric constant for multi-phase flow decomposition.

In the preferred embodiment, frequency transition points (markers) are first identified. As the effective dielectric constant changes as a function of frequency, points at which there are sharp transitions in the effective dielectric constant can be identified to calculate the effective dielectric constant from a given frequency, volume fraction of each phase, and electrical properties of the mixture. For example, this can be accomplished by using the electrical properties of each single phase alone, and then applying the MWS effect for the mixture based on the volume fraction range for each phase in the mixture. Another method of identifying the frequency transition points involves running a sweep frequency signal of different frequency components and identifying frequency points where the effective dielectric constant of a mixture undergoes a sharp transition. After the frequency points are identified, frequency markers are assigned. A frequency marker is an excitation signal composed of one frequency above and below the identified transition point. For multiple transition points, multiple markers can be used. Each frequency marker measures the capacitance at a frequency above and below a transition point. The difference in measured capacitance at different frequency markers is related to the volume fraction of the phase that introduced this frequency transition phenomenon in the effective dielectric value. As each phase has different electrical properties, the points at which each phase contributes to a sharp transition in the effective dielectric constant of the whole mixture is distinct in the frequency domain, as is the identification of frequency markers for each phase.

The measurements of capacitance difference for each phase marker are used to reconstruct 3D images of phase distribution in the imaging domain. Following this approach, one can obtain more than one phase distribution image, each corresponding to a different phase. The number of different phase distribution images that can be obtained from the phase separation approach depends on the number of frequency transition points and phase markers identified. Each single phase volume image can then be used to reconstruct a global image where all phases are visible.

The need for a phase separation method is eminent in capacitance tomography. As capacitance measurements are related to the effective dielectric constant between sensor plates, a maximum of two phases can be imaged when capacitance measurements at a single frequency are used. Moreover, a number of physical properties can't be inferred directly from the conventional capacitance imaging method. For example, the velocity of each phase in a multiphase flow system varies based on the physical properties of each phase. It is desirable to measure the velocity of each phase to better control and understand the processes being measured. Capacitance based imaging provides a velocity measurement of the mixture, but not of each phase alone. For applications that involve mass flow gauging (i.e. oil logging and transportation in pipelines or solids/liquid mass flow rates in fluidized beds) or those requiring a distinction between velocities of different phases, conventional capacitance sensors fall short. The phase separation method developed here fills the gap by providing a method of imaging and measuring each phase independently, fulfilling a practical need for phase separation of multi-phase flow. Other applications that can utilize this technology are multiphase processes that use catalysts and imaging of the human body. Both of those examples involve phases that are conductive, thus enabling this phase separation approach. However, in cases where different layers are layered rather than mixed, the disclosed approach may be used to identify boundaries between phases. For example, applications that involve the human body where tissues of different properties are layered, the disclosed invention can be used to isolate each layer of similar tissues based on identifying its boundaries.

The present invention provides an innovative ECVT sensor and supporting features for multi-phase flow decomposition based on multi-frequency application. This decomposition utilizes ECT, ECVT, or AECVT sensors with a data acquisition unit that can measure capacitances at different frequencies. In the preferred arrangement, a signal of multiple frequencies is sent to the sensing plate. The receiving plate employs several synchronous demodulations in parallel to measure the current at the receiving plate at each frequency. The phase decomposition method is then employed to extract information and generate volume images of each phase individually. The frequencies that correspond to a specific phase are identified based on electric properties of that phase, and other mixing phases in the multiphase flow system. As each phase has different electrical properties, the points at which each phase contributes to a sharp transition in the effective dielectric constant of the whole mixture is distinct in the frequency domain, as is the identification of frequency markers for each phase.

The present invention also provides a method for identifying boundaries between different phases in the layered structure. For example, the human body is formed from different layers (skin, fat, bone etc.) that are layered from the outside inward. As different layers have different electrical properties (dielectric constant and conductivity), the MWS effect will take place at the interface between said layers. The phase decomposition method can be used to identify boundaries between layers for better imaging. Those boundaries can also be integrated in a global volume image where all phases are viewed simultaneously. The integrative and adaptive data acquisition method is used to activate the ECVT sensor plates with different frequencies for detection and volume identification of rusted steel or broken steel cable strands.

An Adaptive data acquisition system can be extended to a new formation that enables simultaneous capacitance measurement of capacitance at different frequencies, as depicted in FIG. 3. Technical features of the system reported in PCT/US14/24457 can also be applied to the current formation of block diagrams in the new formation reported in this pattern.

In (Ser. No. 14/564,204), a dual frequency approach was devised to image steel rust in tendons. The present invention is different in the following ways: 1) it employs more than two frequencies to detect multiple phases in the flow (in prior technology only a single phase was addressed); 2) it devises a method to establish frequency markers based on knowledge of electrical properties for different phases; 3) a method is also devised to quantify phases based on MWS effect; 4) image reconstruction:

a—Capacitance is measured at all frequency markers for all combinations of plate formations;

b—An image is reconstructed using any available reconstruction (algebraic or optimization) technique for each set of capacitance measurements corresponding to a specific frequency;

c—Each pixel or voxel (volume pixel) corresponding to the same location in all reconstructed images is considered for phase decomposition in that voxel. Here, the effective dielectric constant reconstructed at each image will change based on the frequency used to measure the capacitance and generate the image;

d—The difference between effective dielectric constant in voxels located in the same location of each reconstructed image (across all images) is used to identify each phase volume fraction. Here, the effective dielectric constant for a well-mixed multiphase flow system is formulated by relating the effective dielectric constant to the electric properties of phases, the frequency used to measure capacitance, and the volume fraction of each phase. Since all involved parameters are known expect for each phase volume fraction, a number of equations is formed for each voxel location. The number of those equations is equal to the number of frequency points at which measurements were conducted. The set of equations is then solved to calculate the volume fraction of each phase for every voxel (this will allow quantification of the percentage of volume occupied by each phase in the voxel);

e—The process in d is repeated for each voxel location across all images reconstructed for capacitance measurements at different frequencies. Here, volume fraction of each phase is calculated at each voxel location, combining the volume fraction of a single phase in all voxel locations provides a volume image of that phase alone;

f—This phase decomposition process starts with a set of images reconstructed at different frequencies and ends at the same number of images, but each one corresponding to a single phase only. Individual phase volume fractions for each pixel (voxel) are combined together to form an image of that single phase alone. See steps above.

BRIEF DESCRIPTION OF THE DRAWINGS

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Figure 1B:
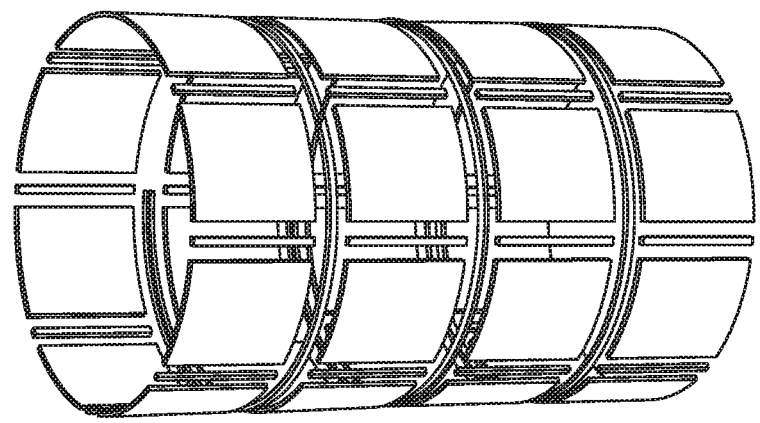
FIG. 1B illustrates one embodiment of the sensor of the present invention.
Figure 1A:
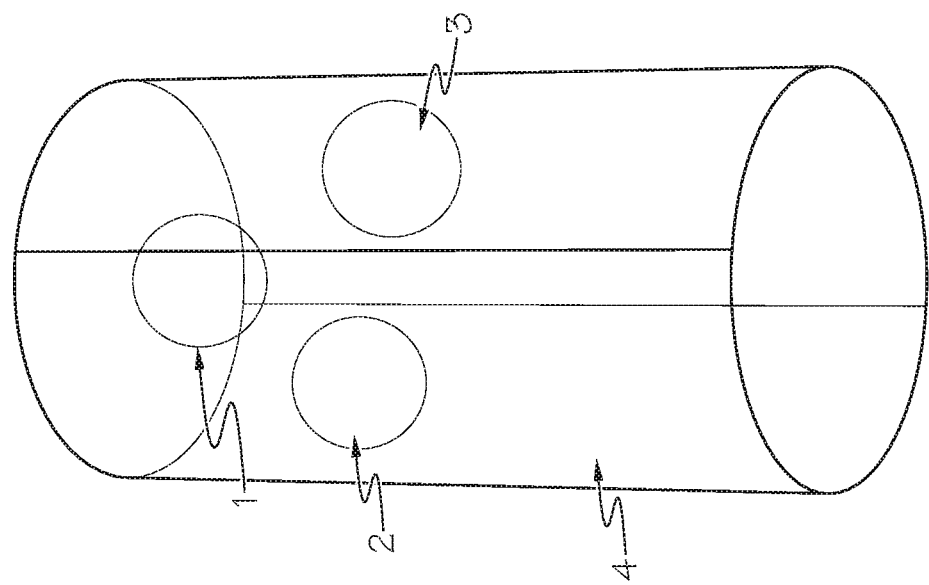
FIG. 1A illustrates one embodiment of three phases each having different electrical properties, in a background of a continuous phase.

FIG. 1A illustrates one embodiment of three phases (1,2,3) each having different electrical properties, in a background of a continuous phase (4). FIG. 1B illustrates one embodiment of the sensor of the present invention. In one embodiment, the sensor is comprised of 24 plates. Each phase component will affect the effective dielectric constant of the mixture and introduce a frequency dependent response based on the electrical properties of the phases and the background.

Figure 2:
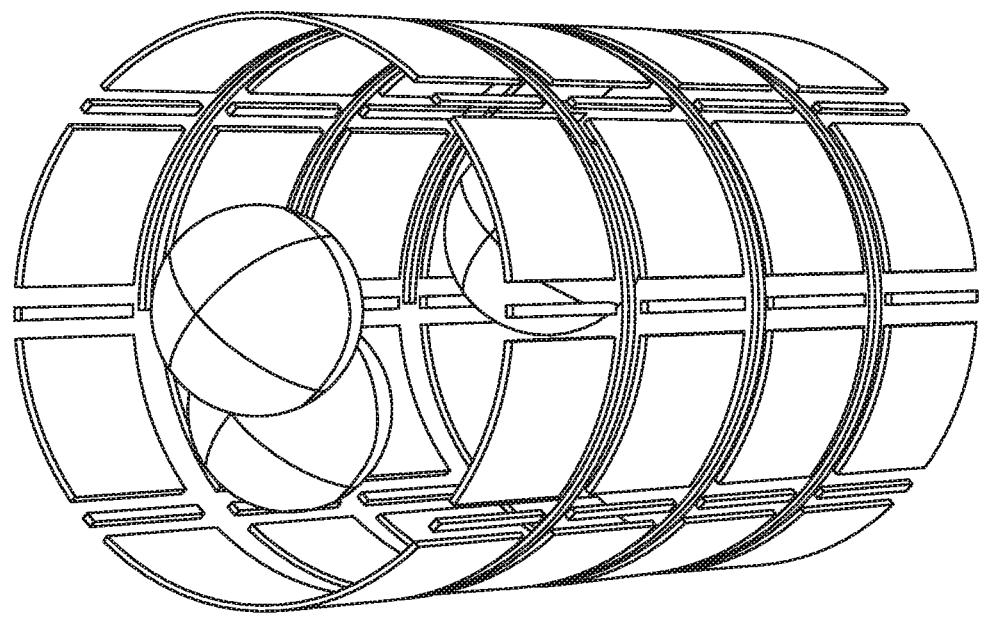
FIG. 2 illustrates the embodiment of the sensor of FIG. 1B with the multi-phase flow components inside.

FIG. 2 illustrates the embodiment of the sensor of FIG. 1B with the phases inside. As the flow evolves, the multi-phase components move inside the sensor. Capacitance measurements between different plate combinations will also change in response to multiphase flow motion. A phase in the multiphase flow will also cause the capacitance to change as a function of frequency. This change is related to that phase concentration, volume fraction, and electrical properties.

Figure 3:
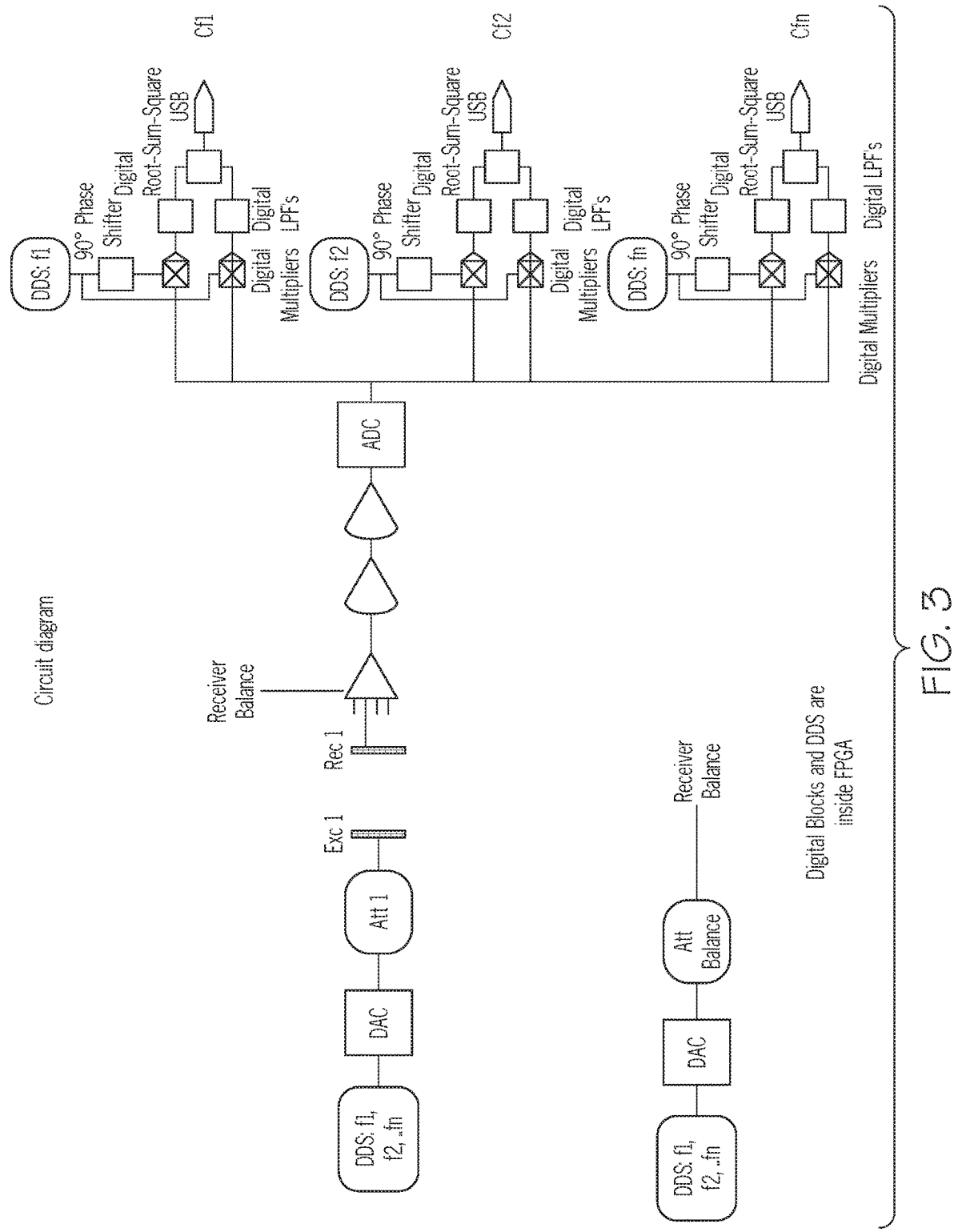
FIG. 3 illustrates one embodiment of the data acquisition design for measuring capacitance at various frequencies, simultaneously.

FIG. 3 illustrates one embodiment a circuit diagram of the present invention. In this configuration, one receiver channel is used with multiple synchronous demodulation paths, each for a specific frequency. The outputs of this circuit are capacitance values acquired at the same time, and at different frequencies.

Figure 4:
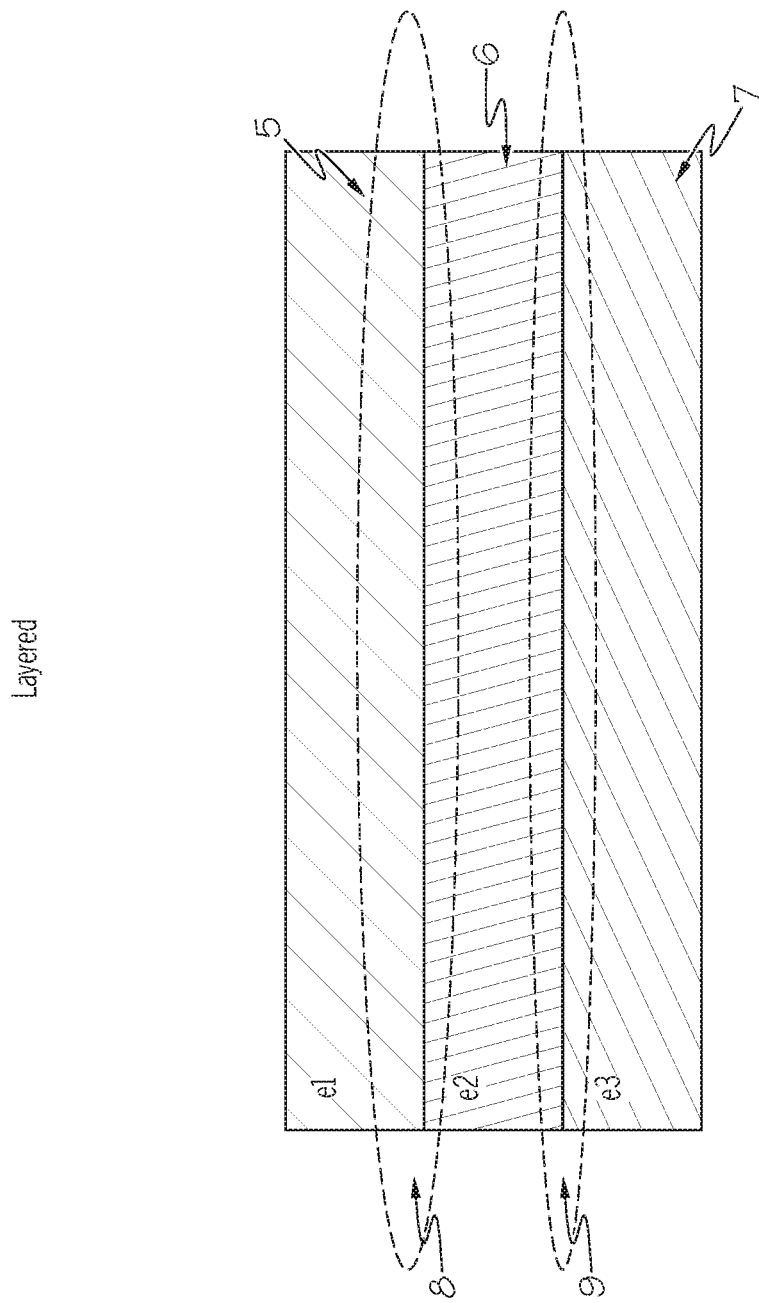
FIG. 4 illustrates one embodiment of the multiphase structure organized in a layered formation.

FIG. 4 illustrates one embodiment of a layered structure, with each layer having different electrical properties (dielectric constant and conductivity). In this structure, the interface between layers will react differently to various frequencies. The result is a capacitance signal that will change as a function of frequency. Knowing the electrical properties of the structure, the MWS effect happens at the interface between materials of different electrical properties. For layered materials, this effect would happen only at the interface between layers. The different in capacitance measurements in this case corresponds to the interfaces at which the effective dielectric constant changes with frequency. Such ability would be of use for applications that employ layered structures, like medical applications.

FIG. 4 illustrates the multiphase flow decomposition approach in identifying and imaging boundaries between materials with different electrical properties as the MWS effect also takes place on the boundaries of such materials. Here, 5 and 7 are materials with different electrical properties (Dielectric constant and conductivity) and 6 is a third material of also different electrical properties sandwiched between 5 and 7. Here also, 8 and 9 are the boundaries between the three layers where the response of the capacitance sensor changes as function of applied frequency. The boundary regions will respond to frequency even if the capacitance for each layer alone (5, 6, and 7) is static with respect to frequency. In this arrangement, the frequency markers approach can be used to identify and image boundaries between layered materials of different properties.

Figure 5:
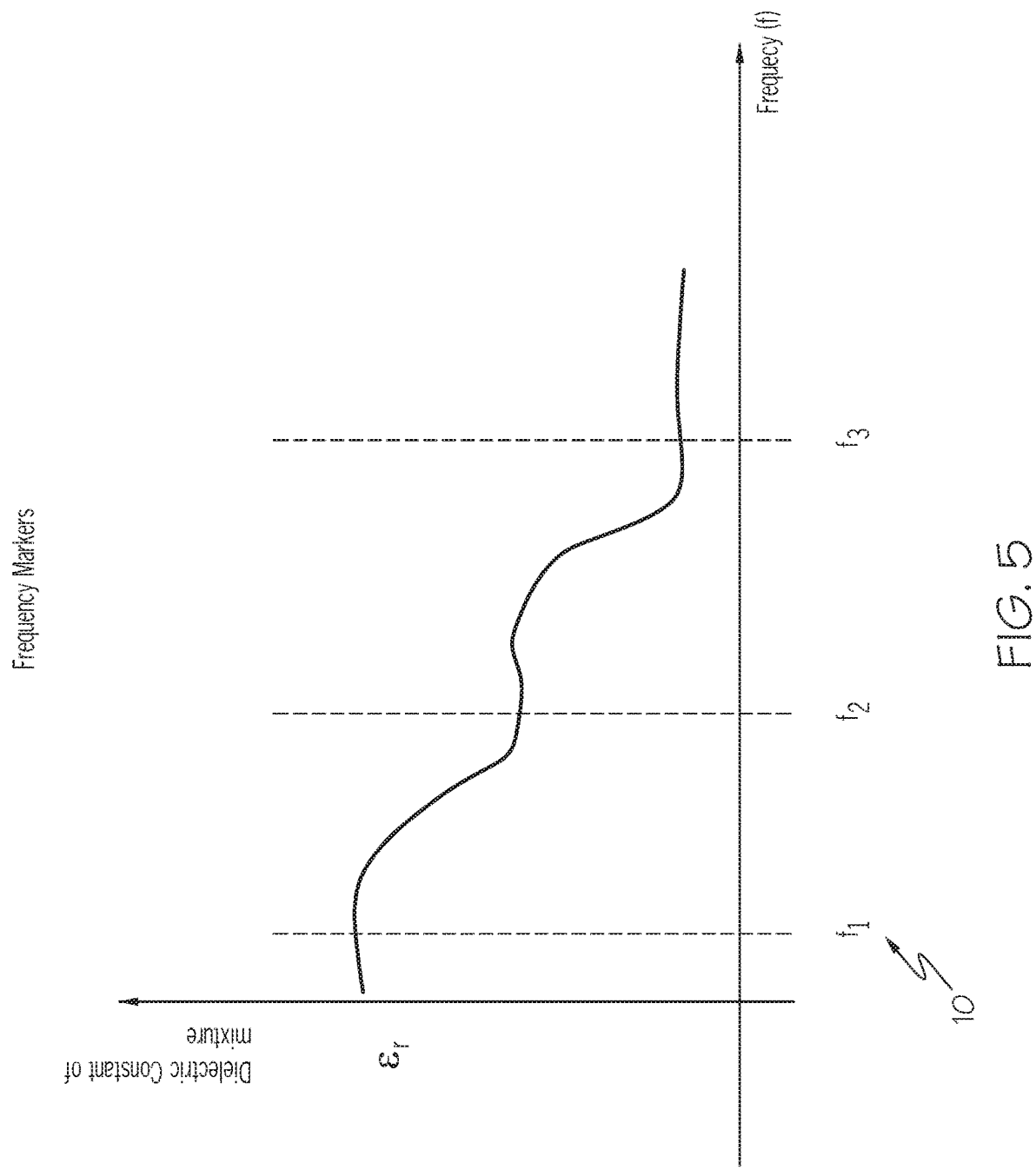
FIG. 5 illustrates one embodiment of frequency markers established for a three phase system, with two phases having electrical conductivity.

FIG. 5 illustrates a typical chart of dielectric response of a multiphase flow mixture to frequency. The points at which the effective dielectric constant of the mixture change are related to the electrical properties of each phase in the multiphase flow mixture. From observing the change in effective dielectric constant by measuring the frequency, the volume of each phase can be inferred. Conducting such measurements using an ECVT sensor would enable the imaging of each phase independently. This figure also shows the identification of frequency markers (f1 shown at 10). A frequency marker is a one that precedes or follows a region of drastic change in the effective dielectric constant of a mixture. By plotting the effective dielectric constant as function of frequency, sharp transitions can be observed. The number of sharp transitions is dependent on the number of phases involved, as depicted in this figure. A capacitance measurement is conducted between two transitions, those points referred to as frequency markers. Acquiring capacitance measurements at such markers provides capacitance data that can be used to image each phase in the multiphase flow independently.

Figure 6:
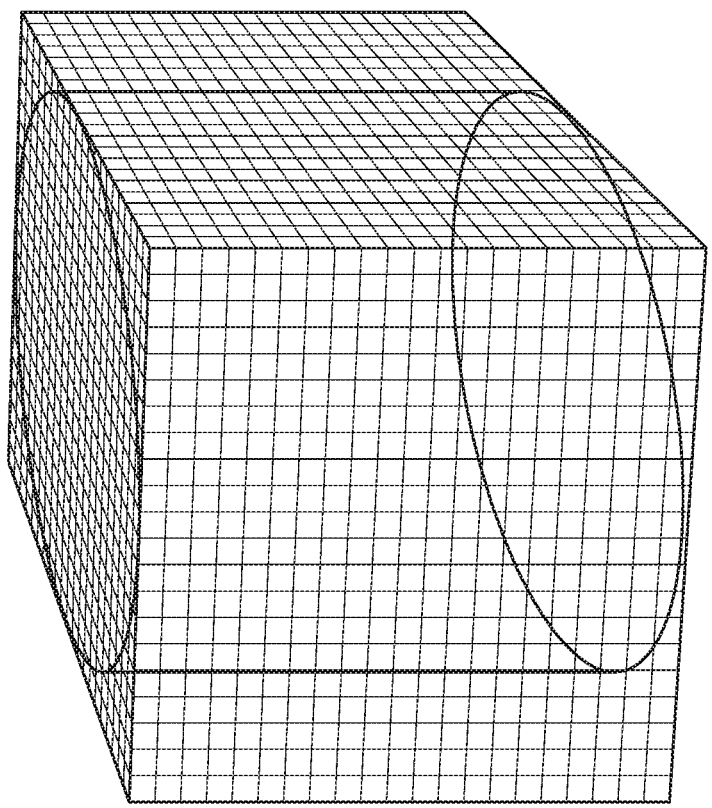
FIG. 6 illustrates one embodiment of an image with multiple voxels. This figure shows how a volume in an image is digitized in small cells or voxels. Applying phase decomposition method entails considering each voxel as a well-mixed cell where each phase is distributed homogeneously across the voxel according to its volume fraction.

FIG. 6 illustrates a typical digitization of an image with each cell representing a voxel. Each voxel in the multi-phase flow decomposition approach is assumed to be well mixed. "Well mixed" means each phase is homogenously distributed in that voxel, according to its volume fraction. For example, if two phase are in a voxel, one has 0.3 volume fraction and the other is 0.7, the first phase is equally distributed in the voxel such that it occupies 30% of the volume of the voxel. The second phase is also equally distributed in the voxel such that it occupies 70% of the voxel volume. In other words, each phase exists in every part of the voxel, with its concentration depending on its volume fraction. The volume fraction of each phase is solved, in each voxel. Voxels are then combined with volume fractions of each phase, generating multiple images each for a single phase.

Figure 7:
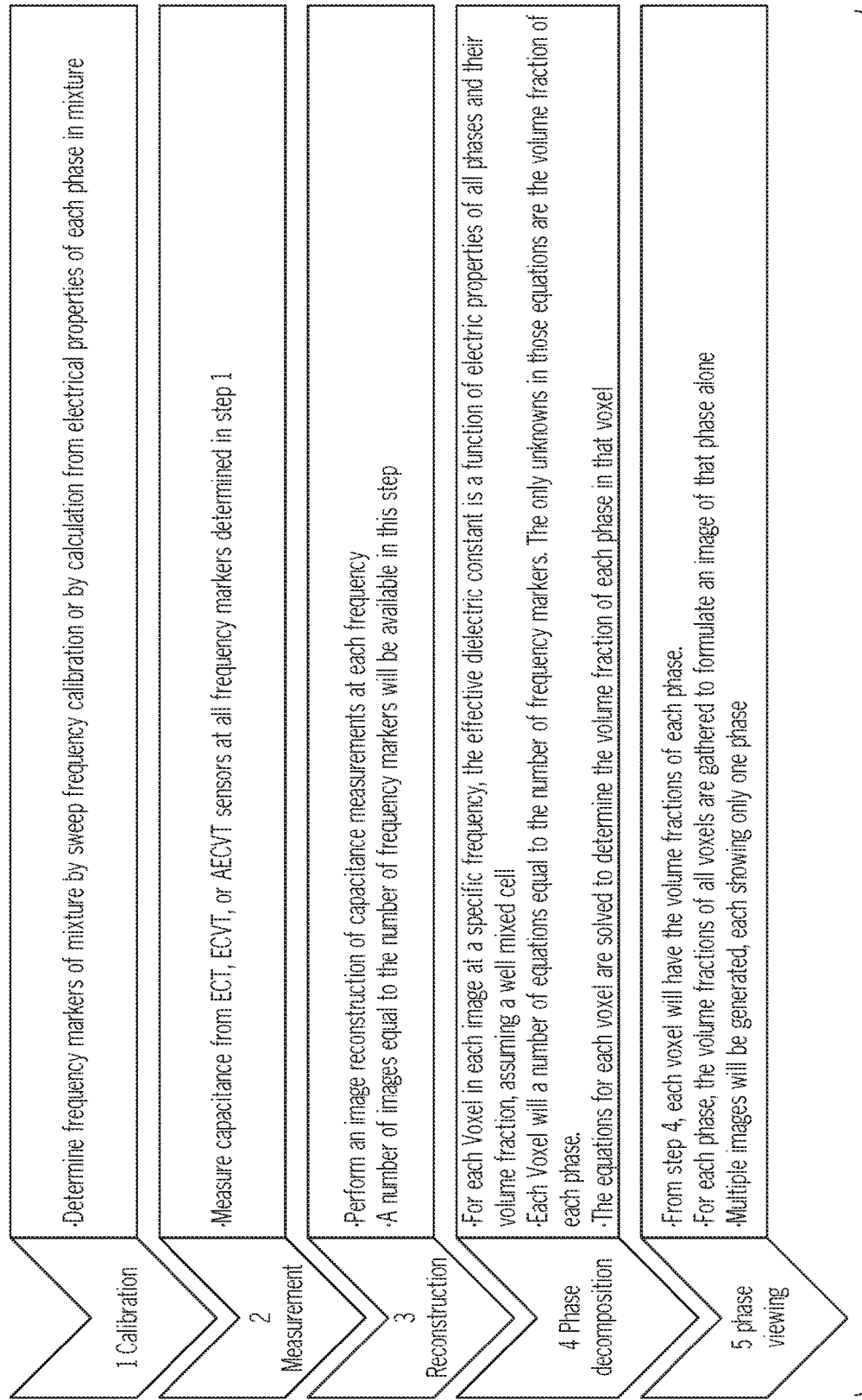
FIG. 7 a flow chart that explains the process of multiphase flow decomposition.

FIG. 7 illustrates a flow chart that describes the steps of implementing the multi-phase flow decomposition approach for one embodiment of the invention. The steps are preferably comprised of calibration, measurement, reconstruction, volume fraction solving, and phase decomposition.

Figure 8:
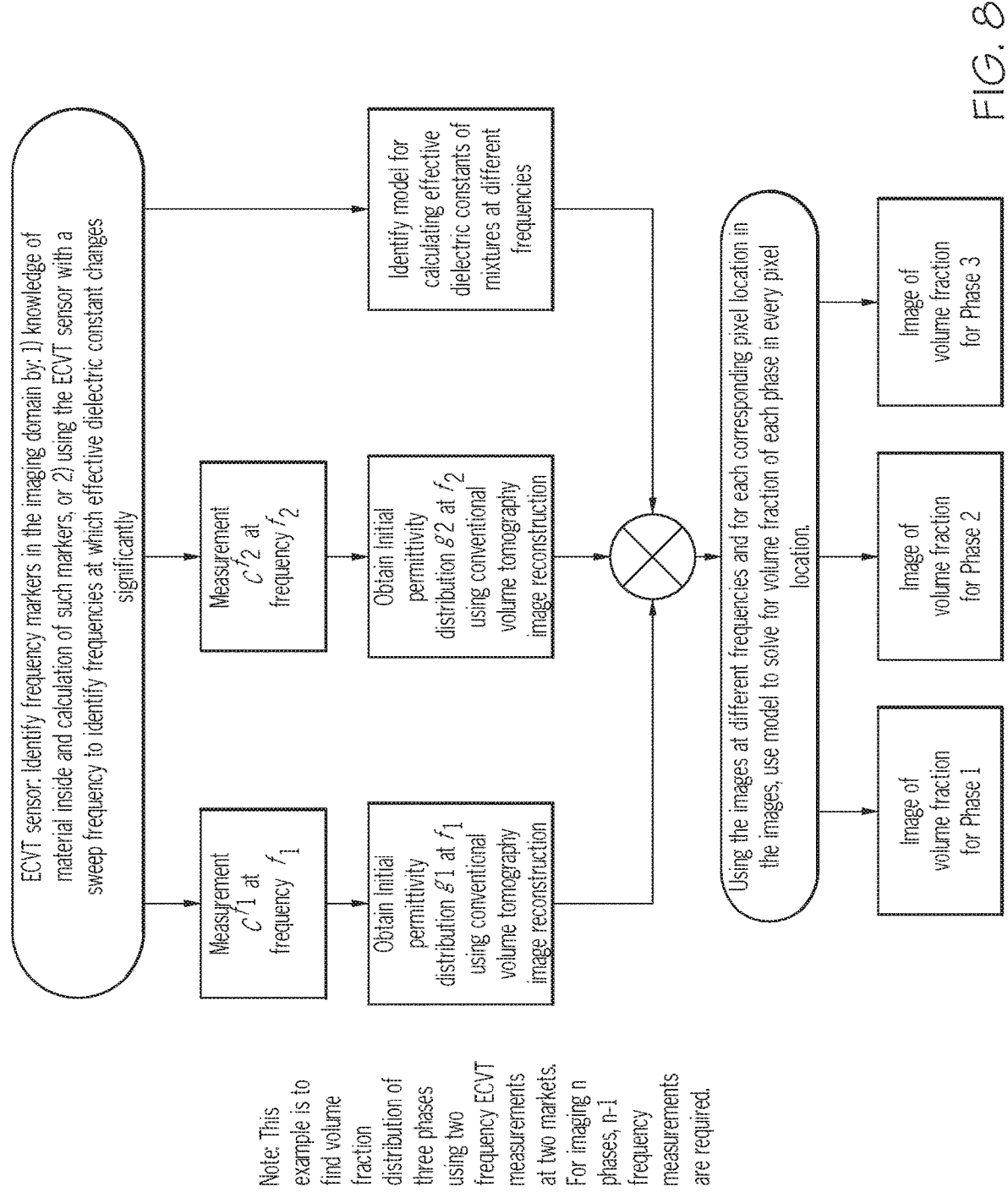
FIG. 8 is a flow chart describing an example process of finding volume fraction distribution of three phases for image volume fraction construction.

FIG. 8 illustrates an example flow chart describing the steps of obtaining the volume fraction distribution of three phases using two frequency ECVT measurements at two markers. For imaging N phases, N−1 frequency measurements are required.

While certain embodiments of the present invention are described in detail above, the scope of the invention is not to be considered limited by such disclosure, and modifications are possible without departing from the spirit of the invention as evidenced by the following claims.

What is claimed is:

1. A system for generating a three-dimensional tomography of a vessel interior or other object and for multi-phase flow decomposition, the system comprising:
   a capacitance sensor comprising a plurality of electrodes for placement around the vessel or the object, wherein the capacitance sensor is adapted to provide electric field distribution and sensor sensitivity in three geometric dimensions;
   data acquisition circuit in communication with the capacitance sensor for receiving input data from the capacitance sensor, the data acquisition circuit adapted to output electric phase signals at different frequencies;
   a hardware processing system in communication with the data acquisition circuit, the hardware processing system programmed with instructions for executing on the hardware processing system to: 1) measure electric phase shift in degrees or radians between an input signal to the sensor and the current produced at an output of the capacitance sensor at all of the different frequencies; 2) reconstruct a three-dimensional volume image from the electric phase shift measured at all of the different frequencies.

2. The system for generating a three-dimensional tomography of a vessel interior or other object and for multi-phase flow decomposition according to claim 1, wherein the hardware processing system is programmed with instructions for executing on the hardware processing system to reconstruct volume images of each phase alone.

3. The system for generating a three-dimensional tomography of a vessel interior or other object and for multi-phase flow decomposition according to claim 2, wherein a reconstructed image based on the electric phase difference is directly related to the phase.

4. The system for generating a three-dimensional tomography of a vessel interior or other object and for multi-phase flow decomposition according to claim 1, wherein the hardware processing system is programmed with instructions for executing on the hardware processing system to reconstruct images of the real or imaginary components of effective dielectric constant at each frequency.

5. The system for generating a three-dimensional tomography of a vessel interior or other object and for multi-phase flow decomposition according to claim 1, wherein the hardware processing system is programmed with instructions for executing on the hardware processing system to reconstruct a plurality of images, each with a single-phase volume fraction image.

6. The system for generating a three-dimensional tomography of a vessel interior or other object and for multi-phase flow decomposition according to claim 1, wherein the hardware processing system is programmed with instructions for executing on the hardware processing system to obtain volume fractions of each phase for each voxel.

7. The system for generating a three-dimensional tomography of a vessel interior or other object and for multi-phase flow decomposition according to claim 6, wherein the hardware processing system is programmed with instructions for executing on the hardware processing system to combine pixels for a single phase volume fraction to formulate an image for the phase.

8. The system for generating a three-dimensional tomography of a vessel interior or other object and for multi-phase flow decomposition according to claim 1, wherein the data acquisition circuit is adapted to output capacitance signals for each of the different frequencies wherein the hardware processing system is programmed with instructions for using the output capacitance or electric phase signals for each of the different frequencies to reconstruct the three-dimensional volume image.

9. The system for generating a three-dimensional tomography of a vessel interior or other object and for multi-phase flow decomposition according to claim 8, wherein the hardware processing system is programmed with instructions for generating volume images of each phase of the multi-phase flow individually.

10. A system for generating a three-dimensional tomography of a vessel interior or other object and for multi-phase flow decomposition, the system comprising:

a capacitance sensor comprising a plurality of electrodes for placement around the vessel or the object, wherein the capacitance sensor is configured to provide sensor sensitivity in three geometric dimensions;

data acquisition circuit in communication with the capacitance sensor for receiving input data from the capacitance sensor, the data acquisition circuit adapted to output capacitance signals and electric phase signals at different frequencies;

a hardware processing system in communication with the data acquisition circuit, the hardware processing system programmed with instructions for executing on the hardware processing system to: 1) measure electric phase shift in degrees or radians between an input signal to the capacitance sensor and the current produced at an output of the capacitance sensor at all of the different frequencies; 2) reconstruct a three-dimensional volume image from the electric phase shift measured at all of the different frequencies.

11. The system for generating a three-dimensional tomography of a vessel interior or other object and for multi-phase flow decomposition according to claim 10, wherein the hardware processing system is programmed with instructions for executing on the hardware processing system to reconstruct volume images of each phase alone.

12. The system for generating a three-dimensional tomography of a vessel interior or other object and for multi-phase flow decomposition according to claim 11, wherein a reconstructed image based on the electric phase difference is directly related to the phase.

13. The system for generating a three-dimensional tomography of a vessel interior or other object and for multi-phase flow decomposition according to claim 10, wherein the hardware processing system is programmed with instructions for executing on the hardware processing system to reconstruct images of the real or imaginary components of effective dielectric constant at each frequency.

14. The system for generating a three-dimensional tomography of a vessel interior or other object and for multi-phase flow decomposition according to claim 10, wherein the hardware processing system is programmed with instructions for generating volume images of each phase of the multi-phase flow individually.

* * * * *